(12) United States Patent
Donners

(10) Patent No.: US 12,171,204 B2
(45) Date of Patent: Dec. 24, 2024

(54) LIGHT GENERATING SYSTEM FOR ARTHROPOD KEEPING

(71) Applicant: SIGNIFY HOLDING B.V., Eindhoven (NL)

(72) Inventor: Maurice Alexander Hugo Donners, Waalre (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 377 days.

(21) Appl. No.: 17/476,517

(22) Filed: Sep. 16, 2021

(65) Prior Publication Data

US 2022/0087234 A1    Mar. 24, 2022

(30) Foreign Application Priority Data

Sep. 18, 2020  (EP) ..................................... 20196832

(51) Int. Cl.
*A01K 67/00* (2006.01)
*A01K 61/59* (2017.01)
(Continued)

(52) U.S. Cl.
CPC .......... *A01K 67/0338* (2013.01); *A01K 61/59* (2017.01); *A01K 63/06* (2013.01);
(Continued)

(58) Field of Classification Search
CPC ........ A01K 67/03; A01K 61/59; A01K 63/06; H05B 45/10; H05B 45/20; H05B 47/155
See application file for complete search history.

(56) References Cited

U.S. PATENT DOCUMENTS

| 2013/0152864 A1 | 6/2013 | Grajcar et al. |
| 2014/0160735 A1* | 6/2014 | Axelrod ................. A01K 63/06 |
| | | 362/101 |

(Continued)

FOREIGN PATENT DOCUMENTS

| CN | 107581125 A | 1/2018 |
| KR | 2019127223 A | 11/2019 |

(Continued)

OTHER PUBLICATIONS

M. Baloi, et al., "Performance of Pacific White Shrimp *Litopenaeus vannamei* Raised in Biofloc Systems With Varying Levels of Light Exposure", Aquacultural Engineering 52, 2013, pp. 39-44.

(Continued)

*Primary Examiner* — Joshua J Michener
*Assistant Examiner* — Henry Hooper Mudd

(57) ABSTRACT

The invention provides a light generating system for arthropod keeping, configured to generate system light, wherein in a first operational mode the light generating system is configured to provide the system light having a spectral power distribution, wherein the spectral power distribution comprises: a first spectral power $E_1$ in a first wavelength range of 360-780 nm; a second spectral power $E_2$ in a second wavelength range of 360-400 nm; a third spectral power $E_S$ in a third wavelength range of 400-480 nm; a fourth spectral power $E_M$ in a fourth wavelength range of 480-580 nm; a fifth spectral power $E_L$ in a fifth wavelength range of 580-700 nm; a sixth spectral power $E_6$ in a sixth wavelength range of 620-700 nm; a seventh spectral power $E_7$ in a seventh wavelength range of 700-780 nm; and wherein: $1.75 \leq E_M/E_S \leq 20$; $E_2/E_1 \leq 0.005$; $E_7/E_1 \leq 0.022$; and $E_L/E_1 \leq 0.3$; or $0.3 < E_L/E_1 \leq 0.8$, and $3.4 \leq E_6/E_S \leq 14$, and wherein the sixth wavelength range comprises a peak between 650-690 nm.

15 Claims, 3 Drawing Sheets

(51) Int. Cl.
  *A01K 63/06*      (2006.01)
  *A01K 67/033*     (2006.01)
  *H05B 45/10*      (2020.01)
  *H05B 45/20*      (2020.01)
  *H05B 47/105*     (2020.01)
  *H05B 47/155*     (2020.01)
  *H05B 47/165*     (2020.01)

(52) U.S. Cl.
  CPC ........ *A01K 67/033* (2013.01); *A01K 67/0339* (2013.01); *H05B 45/10* (2020.01); *H05B 45/20* (2020.01); *H05B 47/105* (2020.01); *H05B 47/155* (2020.01); *H05B 47/165* (2020.01); *A01K 2207/35* (2013.01); *A01K 2227/706* (2013.01)

(56) References Cited

U.S. PATENT DOCUMENTS

| | | | |
|---|---|---|---|
| 2016/0353716 A1 | 12/2016 | Tanase et al. | |
| 2018/0310521 A1* | 11/2018 | Guo | A01K 1/03 |
| 2022/0264728 A1* | 8/2022 | Yokoi | H05B 47/16 |
| 2023/0022621 A1* | 1/2023 | Doane | A01K 67/033 |

FOREIGN PATENT DOCUMENTS

| | | |
|---|---|---|
| WO | 2014039823 A1 | 3/2014 |
| WO | 2016116533 A1 | 7/2016 |
| WO | 2018130403 A1 | 7/2018 |
| WO | 2019023800 A1 | 2/2019 |
| WO | 2019092001 A1 | 5/2019 |

OTHER PUBLICATIONS

L.J. Fleckenstein, et al., "Effects of Supplemental LED Lighting on Water Quality and Pacific White Shrimp (*Litopenaeus vannamei*) Performance in Intensive Recirculating Systems", Aquaculture 504, 2019, pp. 219-226.

K. You, et al., "Effects of Different Light Sources and Illumination Methods on Growth and Body Color of Shrimp *Litopenaeus vannamei*", Acquaculture, Mar. 2006, pp. 1-10.

* cited by examiner

LIGHT GENERATING SYSTEM FOR ARTHROPOD KEEPING

FIELD OF THE INVENTION

The invention relates to a light generating system for arthropod keeping. The invention further relates to an arthropod keeping system. The invention further relates to a method for arthropod keeping. The invention further relates to a computer program product.

BACKGROUND OF THE INVENTION

Systems for arthropod keeping are known in the art. For instance, WO2014039823A1 describes a system for enhancing the growth of aquatic life that includes first and second raceways that both extend from an inlet to an outlet with a channel therebetween and hold water. The raceways are in side by side relation and are in fluid communication with one another. The first raceway has a living food source within the water and the second raceway has aquatic life within the water. Lighting assemblies are provided in each raceway to enhance both the living food source and the aquatic life by using predetermined wavelengths of light.

SUMMARY OF THE INVENTION

Many arthropod species, such as shrimps and flies, are being kept, especially farmed. In particular, immature arthropods are typically farmed. Within farming there is a generic tendency and need to improve the efficiency and reliability of the growing phase. The efficiency may correlate with the ability and desire to lower the impact of the main cost drivers, feed, growth rate and mortality. The reliability links to the need to make the harvesting periods predictable, and to have a smooth supply chain in which seasonal dependencies are preferably taken out.

Arthropods may have specific photoreceptors that provide non-visual information to the animals, which photoreceptors could be targeted to increase the health, well-being and productivity of these arthropods. However, generally arthropods may, during keeping, be primarily exposed to no lighting, natural lighting, or regular (human-centric) lighting, which may rather lead to disinvestments and a limited to no ability to steer keeping.

For example, in existing lighting solutions, the amount of radiation in the UV-A range (about the range of 360-400 nm) and, or blue range (about the range of 400-480 nm) may be relatively high for arthropod keeping. In particular, irradiation with UV-A or blue light may lead to disease and mortality.

Hence, it is an aspect of the invention to provide an alternative light generating system, which preferably further at least partly obviates one or more of above-described drawbacks. The present invention may have as object to overcome or ameliorate at least one of the disadvantages of the prior art, or to provide a useful alternative.

Hence, in a first aspect, the invention may provide a light generating system, especially for arthropod keeping. The light generating system may be configured to generate system light (during operation of the system), and especially to provide the system light to an arthropod hosting space. The light generating system may have a first operational mode, especially wherein in the first operational mode the light generating system is configured to provide the system light having a spectral power distribution. In embodiments, the spectral power distribution may comprise a first spectral power $E_1$ in a first wavelength range of 360-780 nm (here, the visible wavelength range is defined as 360-780 nm). In further embodiments, the spectral power distribution may comprise a second spectral power $E_2$ in a second wavelength range of 360-400 nm. In further embodiments, the spectral power distribution may comprise a third spectral power $E_S$ in a third wavelength range of 400-480 nm. In further embodiments, the spectral power distribution may comprise a fourth spectral power $E_M$ in a fourth wavelength range of 480-580 nm. In further embodiments, the spectral power distribution may comprise a fifth spectral power $E_L$ in a fifth wavelength range of 580-700 nm. In further embodiments, the spectral power distribution may comprise a sixth spectral power $E_6$ in a sixth wavelength range of 620-700 nm. In further embodiments, the spectral power distribution may comprise a seventh spectral power $E_7$ in a seventh wavelength range of 700-780 nm. In further embodiments, with regards to the spectral power distribution, $1.75 \leq E_M/E_S \leq 20$. In further embodiments, with regards to the spectral power distribution, $E_2/E_1 \leq 0.005$. In further embodiments, with regards to the spectral power distribution, $E_7/E_1 \leq 0.025$, such as $E_7/E_1 \leq 0.022$, especially $E_7/E_1 \leq 0.015$. In further embodiments, with regards to the spectral power distribution $E_L/E_1 \leq 0.3$; or $0.3 < E_L/E_1 \leq 0.8$, and $3.4 \leq E_6/E_S \leq 14$, wherein the sixth wavelength range comprises a peak between 650-690 nm. Hence, in specific embodiments the invention may provide a light generating system for arthropod keeping, configured to generate system light, wherein in a first operational mode the light generating system is configured to provide the system light having a spectral power distribution, wherein the spectral power distribution comprises: a first spectral power $E_1$ in a first wavelength range of 360-780 nm; a second spectral power $E_2$ in a second wavelength range of 360-400 nm; a third spectral power $E_S$ in a third wavelength range of 400-480 nm; a fourth spectral power $E_M$ in a fourth wavelength range of 480-580 nm; a fifth spectral power $E_L$ in a fifth wavelength range of 580-700 nm; a sixth spectral power $E_6$ in a sixth wavelength range of 620-700 nm; a seventh spectral power $E_7$ in a seventh wavelength range of 700-780 nm; and wherein: $1.75 \leq E_M/E_S \leq 20$; $E_2/E_1 \leq 0.005$; $E_7/E_1 \leq 0.022$; and (i) $E_L/E_1 \leq 0.3$; or (ii) $0.3 \leq E_L/E_1 \leq 0.8$, and $3.4 \leq E_6/E_S \leq 14$, wherein the sixth wavelength range comprises a peak between 650-690 nm.

The invention may provide the benefit that the system light is tailored for efficient keeping of arthropod species. In particular, the animals may use their visual system, including color vision, in finding and selecting feed. Many feed types may be characterized by a high reflectivity at higher wavelengths (yellow, red, brown colored). A spectrum with 5% to 25% of its radiation between ca 580 nm to 700 nm may enable sufficient color vision. However, arthropod eye sensitivity may drop off steeply between 600 and 660 nm, and larval eyes may have an even more limited sensitivity at high wavelengths. Hence, emitting a lot of radiation in this higher wavelength range may be a waste of energy as it may even distort the color vision experience of the animal and may have limited to no non-visual effect on the animals, or even undesired non-visual effects.

Over the time of day, the spectral content of daylight typically varies. By absorption and reflection, daylight under tree canopies is greener than daylight under an open sky or in a winter forest when all leaves have been shed. For arthropods living under tree cover, such as many insects living on the forest floor or for shrimp post-larvae living in a mangrove forest, this means that the light spectrum they experience can show both a daily and a seasonal variation. In particular, the biological clock and calendar of many arthropods may receive their light input from short and medium wavelength sensitive extraretinal opsins, most likely CRY1 and opnG, with maximum sensitivities around 450 nm and 540 nm and FWHM of about 80 nm and 40 nm, respectively. Stimulation of both opsins may enable to influence the biological clock, but for some animals, immature individuals are very sensitive to short wavelength light. In particular, irradiation with excessive quantities of blue light (between about 400 and 480 nm) can lead to disease and mortality. Therefore, the amount of radiation in this wavelength range should be limited.

Arthropods may be farmed together with organisms capable of photosynthesis, such as plants, algae, bacteria or phytoflagellates, usually to be used as feed for the arthropods. Examples are grasshoppers and grass, or shrimps and bio floc or phytoplankton. In these cases, it may be useful to have radiation in the longer wavelength range, but it should be centered around the long wavelength absorption band of the photosynthesis pigment, which may, for example, be about 660 nm. For effective stimulation of photosynthesis, irradiation in the range between 400 nm and 700 nm may be needed (photosynthetically-active radiation, PAR), where the ratio between the radiation in the upper relative to the lower 80 nm should in specific embodiments be in the range of 4-10, i.e., $4 \leq E_6/E_S \leq 10$.

Hence, there may be various criteria, including conflicting criteria, for the selection of a suitable spectral power distribution. The above-defined spectral power distribution may be particularly beneficial as it represents a selection of spectral power values that results in good performance in view of the various criteria.

Hence, the invention may provide a light generating system for arthropod keeping. The term "light generating system" may herein refer to a system comprising one or more light generating devices. In embodiments, the light generating system may be a light generating device. In further embodiments, the light generating system may comprise a plurality of (different) light generating devices, and especially a control system configured to (individually) control the plurality of light generating devices.

Hence, the light generating system may be configured for the keeping of an arthropod. The term "arthropod keeping" may herein refer to the keeping of arthropods for any purpose, including arthropod keeping, but also with regards to conservation efforts, zoos, or as pets. The term arthropod keeping may in embodiments especially refer to arthropod farming. The term "arthropod keeping" may herein refer to the commercial breeding and growing of an arthropod, such as for human consumption, animal feed production, or production of specific substances, such as proteins or medicinal compounds. Arthropods may also be farmed in captivity for agricultural and industrial use, and also as experimental animal (e.g. fruit flies, or many pest insects). The term "arthropod" may herein refer to a member of the phylum Arthropoda, especially a member of the phylum Euarthropoda. In specific embodiments, the arthropod may comprise a species selected from the group comprising Crustacea, such as crabs, lobsters, crayfish or shrimps. In further embodiments, the arthropod may comprise a species selected from the group comprising Hexapoda, especially Insecta, such as a species selected from the group comprising Orthoptera (e.g. grasshoppers), Blattodea (e.g. cockroaches), Coleoptera (e.g. mealworms), Diptera (e.g. black soldier flies) and Lepidoptera (e.g. Silk Worm).

The light generating system may be configured to generate system light, and especially to provide the system light to an arthropod hosting space.

The term "system light" may herein especially refer to the light that is emitted from the system. Hence, in embodiments, the light generating system may comprise a light generating device configured to provide (a component of) system light. In further embodiments, the light generating device may comprise a light source, wherein the light source provides light source light, wherein (at least part of) the light source light is a component of system light. In further embodiments, the light generating device may comprise a converter, such as a phosphor, wherein the converter is configured to convert (at least part of) the light source light to (a component of) system light. In further embodiments, the light generating system may comprise a plurality of light generating devices, wherein the plurality of light generating devices are configured to together provide the system light. The light generating device, especially each of the plurality of the light generating devices, may especially comprise a solid state light source, such as an LED.

The light generating system may especially be configured to provide the system light to an arthropod hosting space. The arthropod hosting space may especially be configured to host an arthropod, especially a plurality of arthropods. In embodiments, the arthropod hosting space may be configured to host a particular arthropod species. However, in further embodiments, the arthropod hosting space may be configured to host a plurality of different arthropod species.

In embodiments, the arthropod hosting space may comprise a (relatively) closed space, such as a water basin, a cage, a crate, or a box. In further embodiments, the arthropod hosting space may comprise a (relatively) open space, such as a pond, a field of grass, or a section of a water body, such as a section of a lake, a sea or an ocean. Hence, the arthropod hosting space may in embodiments be an indoor space, but may in further embodiments be an (open) outdoor space. In specific embodiments, the arthropod hosting space may comprise a greenhouse, especially a tunnel greenhouse.

In embodiments, the system, especially the control system (see below), may have a first operational mode. The term "operational mode" may also be indicated as "controlling mode". The system, or apparatus, or device (see further also below) may execute an action in a "mode" or "operational mode" or "mode of operation". Likewise, in a method an action, stage, or step may be executed in a "mode" or "operation mode" or "mode of operation". This does not exclude that the system, or apparatus, or device may also be adapted for providing another operational mode, or a plurality of other operational modes. Likewise, this does not exclude that before executing the mode and/or after executing the mode one or more other modes may be executed. However, in embodiments a control system (see further also below) may be available, that is adapted to provide at least the operational mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability). Hence, in embodiments, the system may at least have a first operational mode and a second operational mode.

In the first operational mode, the light generating system may be configured to provide system light having a spectral power distribution.

In general, in embodiments, the spectral power distribution may comprise a first spectral power $E_1$ in a first wavelength range of 360-780 nm.

In further embodiments, the spectral power distribution may comprise a second spectral power $E_2$ in a second wavelength range of 360-400 nm. The light in second wavelength range may generally be detrimental to the arthropod. Hence, in further embodiments, $E_2/E_1 \leq 0.01$, such as $\leq 0.005$, especially $\leq 0.001$, including 0. In further embodiments, $E_2/E_1 \geq 0$, such as $\geq 0.00001$, especially $\geq 0.0001$, such as $\geq 0.001$.

In embodiments, the efficiency of the light generating system with regards to providing the system light may be at least 30%, such as at least 40%, especially at least 45%, such as at least 50%, especially at least 55%, such as at least 60%. The phrase "efficiency of the light generating system with regards to providing the system light" may herein refer to the power (in W) of the irradiance with respect to the electrical power (in W) used by the light generating system, especially by the (plurality of) light generating device(s). In specific cases, adding radiation in the second wavelength range may have a positive effect, such as stimulating growth or pigmentation. Hence, in embodiments, $0.004 < E_2/E_1 < 4$, especially $0.008 \leq E_2/E_1 \leq 2$. In such embodiments, the second wavelength range may especially comprise an emission peak between 370 nm and 395 nm.

The arthropod may have a first non-visual/cerebral/extraretinal photoreceptor ("first photoreceptor") (e.g., opsin CRY1) configured to sense light having a wavelength between 400 nm and 480 nm (e.g., a peak at 440 nm with a FWHM of 40 nm) and a second non-visual/cerebral/extraretinal photoreceptor ("second photoreceptor") (e.g., opsin opnG) configured to sense light having a wavelength between (480 nm and 580 nm) (e.g., a peak at 530 nm with a FWHM of 80 nm).

The term "photoreceptor" may herein refer to a biological structure, especially an organ, or especially a cell, comprising a light-sensitive protein involved in the sensing of light. Photoreceptors may mediate light responses as varied as visual perception, phototropism and phototaxis, as well as responses to light-dark cycles such as circadian rhythm and other photoperiodisms. In particular, an animal may receive information on its environment via its photoreceptors, which may influence the animal behavior. Hence, (artificially) stimulating these photoreceptors may result in beneficial behavior of the arthropod, such as the arthropod adopting a beneficial biological clock, or such as the arthropod feeding at desired timepoints.

Hence, in further embodiments, the spectral power distribution may comprise a third spectral power $E_S$ in a third wavelength range of 400-480 nm, which may especially be suitable to excite the first photoreceptor. Light in the third wavelength range may promote feeding, which may enhance growth, but which may also result in more energy being spent on physical activity, respiration and metabolism, which in turn may limit growth. Further, as mentioned above, arthropods, especially immature individuals, may be sensitive to short wavelength light, and irradiation with light in the range of 400-480 nm may lead to disease and mortality. Hence, there may be a trade-off between stimulating feeding and the mentioned detrimental effects.

In further embodiments, the spectral power distribution may comprise a fourth spectral power $E_M$ in a fourth wavelength range of 480-580 nm, which may especially be suitable to excite the second photoreceptor. Light in the fourth wavelength range may especially serve as a second input into the biological clock system. Further, light in the fourth wavelength range may stimulate molting and growth, and may promote maturation and stimulate egg production, which may especially be beneficially provided to adult arthropods. However, light in the fourth wavelength range may be less effective in stimulating (feeding) activity.

Hence, with regards to the third wavelength range and the fourth wavelength range, a balance may need to be identified to in view of the different (positive and negative) effects of the two wavelength ranges, which may be crucial in stimulating physical activity and the biological clock (and thereon dependent physiological/biological processes).

Hence, in embodiments, $1.75 \leq E_M/E_S \leq 30$, especially $2 \leq E_M/E_S \leq 30$, or especially $1.75 \leq E_M/E_S \leq 20$. In further embodiments, $E_M/E_S \geq 1.5$, such as $E_M/E_S \geq 1.75$, especially $E_M/E_S \geq 2$, such as $\geq 2.4$, especially $\geq 3$, such as $\geq 4$. In further embodiments, $E_M/E_S \leq 35$, such as $E_M/E_S \leq 30$, especially $E_M/E_S \leq 20$, such as $E_M/E_S \leq 15$, especially $E_M/E_S \leq 12$, such as $E_M/E_S \leq 11$, especially $E_M/E_S \leq 8$.

In further embodiments, the spectral power distribution may comprise a fifth spectral power $E_L$ in a fifth wavelength range of 580-700 nm. Light in the fifth wavelength range may contribute to the finding and selecting of feed by the arthropod. However, an excess of light in the fifth wavelength range may distort the color vision of the animal, and may be relatively wasteful as the fifth wavelength range may have no non-visual effect on the animal.

Hence, in embodiments, $E_L/E_1 \leq 0.4$, such as $E_L/E_1 \leq 0.30$, especially $E_L/E_1 \leq 0.25$, such as $E_L/E_1 \leq 0.15$, especially $E_L/E_1 \leq 0.11$. In further embodiments, $E_L/E_1 \geq 0.002$, such as $E_L/E_1 \geq 0.01$, especially $E_L/E_1 \geq 0.05$.

In further embodiments, arthropods may be farmed together with other organisms, such as organisms capable of photosynthesis, such as plants, algae, bacteria or phytoflagellates. The other organisms may usually be used as feed for the arthropods, but may also live in symbiosis with the arthropods, especially where the other organisms live on waste products, such as excrements, of the arthropods, or vice versa. In these cases, it may be useful to have radiation in the fifth wavelength range to stimulate photosynthesis. The light in the fifth wavelength range may, in such embodiments, especially be centered around the long wavelength absorption band of a photosynthesis pigment, such as centered about 660 nm. In particular, for effective stimulation of photosynthesis, irradiation in the range between 400 nm and 700 nm may be beneficial (photosynthetically-active radiation, PAR), especially where a ratio of the third spectral power $E_S$ to the sixth spectral power $E_6$ is selected from the range of 4-14, especially from the range of 4-10, or especially from the range of 3.4-14, i.e., $3.4 \leq E_6/E_S \leq 14$, especially wherein $4.75 \leq E_6/E_S \leq 12.5$, such as $5 \leq E_6/E_S \leq 10$. Hence, in further embodiments, $0.3 \leq E_L/E_1 \leq 0.8$, and $3.4 \leq E_6/E_S \leq 14$, and especially wherein the sixth wavelength range comprises a (broad) peak between 650-690 nm.

Hence, in further embodiments, the spectral power distribution may comprise a sixth spectral power $E_6$ in a sixth wavelength range of 620-700 nm.

Hence, when $E_L$ is unequal to zero, the intensity in the $E_L$ range may be solely within the $E_6$ range, solely outside the $E_6$ range, or both within and outside the $E_6$ range.

In further embodiments, the spectral power distribution may comprise a seventh spectral power $E_7$ in a seventh wavelength range of 700-780 nm. However, light in the seventh wavelength range may be harmful to many arthropod species, especially insect species. Hence, in embodiments, $E_7/E_1 \leq 0.08$, such as $E_7/E_1 \leq 0.05$, especially $E_7/E_1 \leq 0.025$, such as $E_7/E_1 \leq 0.022$, especially $E_7/E_1 \leq 0.02$, such as $\leq 0.015$, especially $E_7/E_1 \leq 0.01$, including $E_7/E_1 = 0$. In further embodiments $E_7/E_1 \geq 0$, such as $E_7/E_1 \geq 0.0001$, especially $E_7/E_1 \geq 0.001$, such as $E_7/E_1 \geq 0.01$.

As indicated above, the spectral power distribution may be divided in a plurality of ranges of which specific ranges may be of interest: the first spectral power $E_1$ (in the first wavelength range of 360-780 nm); the a second spectral power $E_2$ (in the second wavelength range of 360-400 nm); the third spectral power $E_S$ (in the third wavelength range of 400-480 nm); the fourth spectral power $E_M$ (in the fourth wavelength range of 480-580 nm); the fifth spectral power $E_L$ (in the fifth wavelength range of 580-700 nm); the sixth spectral power $E_6$ (in the sixth wavelength range of 620-700 nm); and the seventh spectral power $E_7$ (in the seventh wavelength range of 700-780 nm). The spectral power of the spectral power distribution in the visible wavelength range (here defined as 360-780 nm) may be the integrated power over the wavelength range. Hence, in embodiments the total power in the spectral power distribution may be defined as $E_2+E_S+E_M+E_L+E_7$. As indicated above, $E_6$ is included in $E_L$. Herein, at least one of $E_2$, $E_S$, $E_M$, $E_L$, $E_7$ is larger than zero during operation of the light generating system. In particular, at least one of $E_S$ and $E_M$ is larger than zero during operation of the light generating system. In further embodiments, at least two of $E_2$, $E_S$, $E_M$, $E_L$, $E_7$ may be larger than zero during operation of the light generating system, especially at least three, such as at least four, especially all.

In embodiments, the first operational mode may comprise a repeating temporal pattern. The temporal pattern may especially comprise a photoperiod and a dark period. The photoperiod may especially represent a daylight period of the arthropod. Arthropods, especially different arthropod species, may, however, be exposed to very diverse habitats, such as from shallow estuaries to deep sea and from sunny meadows to half-buried under tree canopies. Hence, during the photoperiod the light generating system may be configured to generate the system light at an intensity selected from the range of 0.5-2000 lux. In further embodiments, during the photoperiod, the light generating system may be configured to generate the system light at an intensity of at least 0.2 lux, especially at least 0.5 lux, such as at least 1 lux, especially at least 2 lux, such as at least 5 lux, especially at least 10 lux, such as at least 30 lux, especially at least 50 lux, such as at least 100 lux. In further embodiments, during the photoperiod, the light generating system may be configured to generate the system light at an intensity of at most 2500 lux, such as at most 2000 lux, especially at most 1500 lux, such as at most 1000 lux, especially at most 500 lux, such as at most 200 lux, especially at most 100 lux.

During the dark period, the light generating system may be configured to generate the system light at an intensity selected from the range of 0-0.5 lux. In further embodiments, during the dark period, the light generating system may be configured to generate the system light at an intensity of at least 0 lux, such as at least 0.01 lux, especially at least 0.1 lux, such as at least 0.2 lux. In further embodiments, during the dark period, the light generating system may be configured to generate the system light at an intensity of at most 5 lux, such as at most 2 lux, especially at most 1 lux, such as at most 0.5 lux, especially at most 0.4 lux, such as at most 0.2 lux.

In specific embodiments, during the dark period the average intensity (averaged in time) is at least 20 times smaller than an average intensity during the photoperiod, such as at least 60 times smaller, especially at least 200 times smaller, such as at least 1000 times smaller.

When intensities in lux are indicated, the intensity especially refers to illuminance. Otherwise, intensities may refer to Watts, like especially in the case of spectral power distributions.

Artificially expanding the length of the photoperiod—relative to the photoperiod an arthropod is naturally exposed to—may lead to higher growth performance. In particular, expanding the length of the photoperiod relative to the dark period may lead to higher growth performance. However, there may be diminishing returns, i.e., the relative benefit of a small increase in the photoperiod may be larger than that of a large increase in the photoperiod, such as by effectively removing the dark period. In addition, reducing the photoperiod length may reduce overall lighting requirements, which may be beneficial in terms of costs and environmental footprint. Hence, the selection of a duration of the temporal pattern, and of the relative durations of the photoperiod and the dark period may be made in view of these (optimization) criteria.

Hence, in further embodiments, the temporal pattern may have a pattern duration $T_p$ selected from the range of 8-30 hours, especially from the range of 12-24 hours, such as from the range of 12-16 hours, or such as from the range of 16-24 hours.

In further embodiments, the photoperiod may have a photoperiod duration $T_d$, wherein $0.35 \leq T_d/T_p \leq 0.9$, such as $0.40 \leq T_d/T_p \leq 0.75$, especially $0.45 \leq T_d/T_p \leq 0.75$, such as $0.50 \leq T_d/T_p \leq 0.75$. Hence, in further embodiments, $T_d/T_p \geq 0.3$, such as $\geq 0.35$, especially $\geq 0.4$, such as $\geq 0.45$, especially $\geq 0.5$, such as $\geq 0.55$. In further embodiments, $T_d/T_p \leq 0.9$, especially $T_d/T_p \leq 0.8$, such as $T_d/T_p \leq 0.75$, especially $T_d/T_p \leq 0.7$, such as $T_d/T_p \leq 0.65$, especially $T_d/T_p \leq 0.6$. Note that the photoperiod duration $T_d$ plus the duration of the dark period is the pattern duration $T_p$.

Such durations of a photoperiod and a dark period may be beneficial for the efficiency of arthropod keeping, such as in view of arthropod growth.

The term "repeating temporal pattern" may especially refer to a plurality of successively arranged temporal patterns that each comprise a pattern duration $T_p$ selected from the range of 8-30 hours, and that each have a photoperiod duration $T_d$, wherein $0.35 \leq T_d/T_p \leq 0.75$. The plurality of successively arranged temporal patterns may be similar, especially (essentially) the same.

However, in further embodiments, successively arranged temporal patterns may gradually vary, such as gradually increase (or decrease) in the (relative) duration of the photoperiod. A gradual in- or decrease of photoperiod can signal a (coming) change of season to the animal, provoking or preventing physiological changes such as accelerated growth and development, pupation or maturation.

In further embodiments, the photoperiod may comprise alternating feeding periods and non-feeding periods, wherein the feeding periods have a duration selected from the range of 10-60 min, and wherein the non-feeding periods have a duration selected from the range of 60-300 min, especially wherein $E_M/E_S$ is lower during the feeding period than during the non-feeding period. As indicated above, light in the third wavelength range may promote feed intake, which may be beneficial for growth, but may further result in increased activity and associated energy expenditure, particularly after the animal has finished feeding, which may be detrimental for growth. Hence, by alternating feeding periods and non-feeding periods, the beneficial growth effects of feeding may be attained, while the detrimental effects of the increased energy expenditure may be reduced.

Hence, in such embodiments, the first operational mode may comprise providing system light having the spectral power distribution during the non-feeding period, and the first operational mode may comprise providing (feeding)

system light having a modified (feeding) spectral power distribution during the feeding period.

In further embodiments, during (at least part of) the feeding period, $0.001 \leq E_M/E_S \leq 2$, especially $0.001 \leq E_M/E_S \leq 1.5$, such as $0.001 \leq E_M/E_S \leq 1$. Hence, the modified (feeding) spectral power distribution may be the same as the spectral power distribution, except that $0.001 \leq E_M/E_S \leq 2$. Hence, in embodiments, the modified (feeding) spectral power distribution may be the same as the spectral power distribution, except that the condition $2 \leq E_M/E_S \leq 30$ (which may apply in embodiments) is replaced by the condition $0.001 \leq E_M/E_S \leq 1$. In further embodiments, during (at least part of) the feeding period $E_M/E_S \geq 0.01$, such as $\geq 0.1$. In further embodiments, during (at least part of) the feeding period $E_M/E_S \leq 0.5$, such as $\leq 0.25$. In further embodiments, during (at least part of) the feeding period the first operational mode may comprise providing the modified (feeding) spectral power distribution. In further embodiments, during (at least part of) the feeding period the first operational mode may comprise providing the spectral power distribution.

In further embodiments, during (at least part of) the feeding period the ratio $E_M/E_S$ may be at least 2 times smaller than the ratio $E_M/E_S$ during the non-feeding period, especially at least 10 times smaller, such as at least 100 times smaller.

In further embodiments, the photoperiod comprises one or more first photoperiods and a second photoperiod, especially wherein the one or more first photoperiods and the second photoperiod are temporally separated, i.e., nonoverlapping in time. The one or more first photoperiods may be temporally arranged at one or more of the beginning and the end of the photoperiod. The one or more first photoperiods may (each) have a duration selected from the range of 5-120 minutes, such as from the range of 10-90 minutes, especially from the range of 15-60 minutes.

The one or more first photoperiods may especially be temporally separated by the second photoperiod, especially by one or more second photoperiods. During the second photoperiod, the light generating system may especially provide the same system light as during the dark period, but may also provide different system light. In particular, the light generating system may provide a higher lux during the one or more first photoperiods than during the one or more second photoperiods, and may provide a higher lux during the one or more second photoperiods than during the dark period. The one or more second photoperiods may (each) have a duration selected from the range of 5-1500 minutes, such as from the range of 10-1080 minutes, especially from the range of 30-600 minutes, such as from the range of 60-120 minutes.

Hence, in further embodiments, the photoperiod may comprise alternating first photoperiods and second photoperiods, especially wherein the one or more first photoperiods are temporally arranged at (at least) one or more of the beginning and the end of the photoperiod.

In further embodiments, during the one or more first photoperiods, the light generating system may generate the system light at a first intensity $I_1$, and during the second photoperiod the light generating system may generate the system light at a second intensity $I_2$, wherein $1.5 \leq I_1/I_2 \leq 1000$, such as $2 \leq I_1/I_2 \leq 500$. In particular, it may not be necessary to provide light during the entire photoperiod in order to influence the circadian clock of the arthropod. Rather, providing light for relatively short first photoperiods may be sufficient, which may reduce overall lighting requirement, which may be beneficial in terms of costs and environmental footprint.

In further embodiments, the one or more first photoperiods comprises at least two first photoperiods, wherein a first of the at least two first photoperiods is temporally arranged at the beginning of the photoperiod, and wherein a second of the at least two first photoperiods is temporally arranged at the end of the photoperiod.

In embodiments, the light generating system may comprise a light generating device, especially a plurality of light generating devices.

In further embodiments, the plurality of light generating devices may comprise a first light generating device. The first light generating device may especially be configured to provide first radiation having a first peak wavelength in the wavelength range of 420-480 nm. The first light generating device may especially comprise a solid state light source, such as an LED, with an emission spectrum selected so that, taking any absorption and emission from a phosphor into account, it provides first radiation having a first peak wavelength between 420 nm and 480 nm, especially between 440 nm and 460 nm. In further embodiments, the first peak wavelength may lie within 30 nm from the peak sensitivity of the first photoreceptor (e.g., opsin CRY1), especially within 10 nm.

In further embodiments, the plurality of light generating devices may comprise a second light generating device. The second light generating device may especially be configured to provide second radiation having a second peak wavelength in the wavelength range of 500-560 nm. The second light generating device may especially comprise a solid state light source, such as an LED, with an emission spectrum selected so that, taking any absorption and emission from a phosphor into account, it provides second radiation having a second peak wavelength between 500 nm and 560 nm, especially between 520 nm and 550 nm.

In embodiments, the second light generating device may comprise a luminescent material. In specific embodiments, the luminescent material (of the second light generating device) may be selected from the group comprising lutetium comprising $A_3B_5O_{12}$:$Ce^{3+}$ luminescent material (such as $Lu_3Al_5O_{12}$:$Ce^{3+}$, LuAG), lutetium comprising $(Lu_xY_{1-x})_3Al_5O_{12}$:Ce luminescent material (Lime), barium comprising $Ba_2SiO_4$:Eu luminescent material (BOSE), yttrium comprising $A_3B_5O_{12}$:$Ce^{3+}$ (such as $Y_3Al_5O_{12}$:$Ce^{3+}$, YAG), europium comprising $Eu_xSi_{6-z}Al_zO_yN_{8-y}$ (such as y=z−2x, x=0.018, z=0.23, β-SiALON green), and lutetium comprising $(Lu_{1-a-b-c}Y_aTb_bA_c)_3(Al_{1-d}B_d)_5(O_{1-e}C_e)_{12}$:Ce, Eu, (such as where A is selected from the group consisting of Mg, Sr, Ca, and Ba; B is selected from the group consisting of Ga and In; C is selected from the group consisting of F, Cl, and Br; and $0 \leq a \leq 1$; $0 \leq b \leq 1$; $0 \leq c \leq 0.5$; $0 \leq d \leq 1$; and $0 \leq e \leq 0.2$), especially a phosphor selected from the group consisting of BOSE, LuAG and Lime (and similar phosphors).

In further embodiments, the luminescent material may comprise $Si_{6-z}Al_zO_zN_{8-z}$ (such as $0.1 \leq z \leq 2.0$, especially $z \leq 1.0$).

In specific embodiments, the luminescent material may comprise a luminescent material of the type $A_3B_5O_{12}$:Ce, wherein A in embodiments comprises one or more of Y, La, Gd, Tb and Lu, especially (at least) one or more of Y, Gd, Tb and Lu, and wherein B in embodiments comprises one or more of Al, Ga, In and Sc. Especially, A may comprise one or more of Y, Gd and Lu, such as especially one or more of Y and Lu. Especially, B may comprise one or more of Al and Ga, more especially at least Al, such as essentially entirely Al. Hence, especially suitable luminescent materials are cerium comprising garnet materials. Embodiments of garnets especially include $A_3B_5O_{12}$ garnets, wherein A comprises at least yttrium or lutetium and wherein B comprises at least aluminum. Such garnets may be doped with cerium (Ce), with praseodymium (Pr) or a combination of cerium and praseodymium; especially however with Ce. Especially, B comprises aluminum (Al), however, B may also partly comprise gallium (Ga) and/or scandium (Sc) and/or indium (In), especially up to about 20% of Al, more especially up to about 10% of Al (i.e. the B ions essentially consist of 90 or more mole % of Al and 10 or less mole % of one or more of Ga, Sc and In); B may especially comprise up to about 10% gallium. In another variant, B and O may at least partly be replaced by Si and N. The element A may especially be selected from the group consisting of yttrium (Y), gadolinium (Gd), terbium (Tb) and lutetium (Lu). Further, Gd and/or Tb are especially only present up to an amount of about 20% of A. In a specific embodiment, the garnet luminescent material comprises $(Y_{1-x}Lu_x)_3B_5O_{12}$:Ce, wherein x is equal to or larger than 0 and equal to or smaller than 1. The term ":Ce", indicates that part of the metal ions (i.e. in the garnets: part of the "A" ions) in the luminescent material is replaced by Ce. For instance, in the case of $(Y_{1-x}Lu_x)_3Al_5O_{12}$:Ce, part of Y and/or Lu is replaced by Ce. This is known to the person skilled in the art. Ce will replace A in general for not more than 10%; in general, the Ce concentration will be in the range of 0.1 to 4%, especially 0.1 to 2% (relative to A). Assuming 1% Ce and 10% Y, the full correct formula could be $(Y_{0.1}Lu_{0.89}Ce_{0.01})_3Al_5O_{12}$. Ce in garnets is substantially or only in the trivalent state, as is known to the person skilled in the art.

In embodiments, the phosphor may have the formula $(Lu_{1-a-b-c}Y_aTb_bA_c)_3(Al_1-dB_d)_5(O_{1-e}Ce)_{12}$:Ce,Eu, wherein A is selected from the group consisting of Mg, Sr, Ca, and Ba; B is selected from the group consisting of Ga and In; C is selected from the group consisting of F, Cl, and Br; and $0 \leq a \leq 1$; $0 \leq b \leq 1$; $0 \leq c \leq 0.5$; $0 \leq d \leq 1$; and $0 \leq e \leq 0.2$. In specific embodiments the luminescent material comprises $(Y_{x1-x2-x3}A'_{x2}Ce_{x3})_3(Al_{y1-y2}B'_{y2})_5O_{12}$, wherein x1+x2+x3=1, wherein x3>0, wherein $0<x2+x3 \leq 0.2$, wherein y1+y2=1, wherein $0 \leq y2 \leq 0.2$, wherein A' comprises one or more elements selected from the group consisting of lanthanides, and wherein B' comprises one or more elements selected from the group consisting of Ga, In and Sc. In embodiments, x3 is selected from the range of 0.001-0.1.

Instead of the term "luminescent material" also the term "phosphor" may be used. These terms are known to the person skilled in the art.

The term "luminescent material" especially refers to a material that can convert first radiation, especially one or more of UV radiation and blue radiation, into second radiation. In general, the first radiation and second radiation have different spectral power distributions. Hence, instead of the term "luminescent material", also the terms "luminescent converter" or "converter" may be applied. In general, the second radiation has a spectral power distribution at larger wavelengths than the first radiation, which is the case in the so-called down-conversion. In specific embodiments, however the second radiation has a spectral power distribution with intensity at smaller wavelengths than the first radiation, which is the case in the so-called up-conversion.

In embodiments, the "luminescent material" may especially refer to a material that can convert radiation into e.g. visible and/or infrared light. For instance, in embodiments the luminescent material may be able to convert one or more of UV radiation and blue radiation, into visible light. The luminescent material may in specific embodiments also convert radiation into infrared radiation (IR). Hence, upon excitation with radiation, the luminescent material emits radiation. In general, the luminescent material will be a down converter, i.e. radiation of a smaller wavelength is converted into radiation with a larger wavelength ($\lambda_{ex}<\lambda_{em}$), though in specific embodiments the luminescent material may comprise up-converter luminescent material, i.e. radiation of a larger wavelength is converted into radiation with a smaller wavelength ($\lambda_{ex}>\lambda_{em}$).

In embodiments, the term "luminescence" may refer to phosphorescence. In embodiments, the term "luminescence" may also refer to fluorescence. Instead of the term "luminescence", also the term "emission" may be applied. Hence, the terms "first radiation" and "second radiation" may refer to excitation radiation and emission (radiation), respectively. Likewise, the term "luminescent material" may in embodiments refer to phosphorescence and/or fluorescence. The term "luminescent material" may also refer to a plurality of different luminescent materials. Examples of possible luminescent materials are indicated below.

Not only the second light generating device may in embodiments comprise a luminescent material. Alternatively or additionally, in embodiments one or more of the first, the third and the fourth light generating device may comprise a luminescent material. As will be understood, these phosphors may differ, as the spectral power distributions of the device light of the first, second, third, and fourth light generating devices may differ.

In further embodiments, the plurality of light generating devices may comprise a third light generating device. The third light generating device may be configured to provide third radiation having a third peak wavelength in the wavelength range of 570-630 nm, especially in the wavelength range of 570-600, or especially in the wavelength range of 600-630. In further embodiments, the third light generating device may comprise a direct or phosphor-converted amber LED, especially wherein the third light generating device is configured to provide third radiation having a third peak wavelength in the wavelength range of 570-600 nm. In further embodiments, the third light generating device may comprise a direct or phosphor-converted red-orange LED, especially wherein the third light generating device is configured to provide third radiation having a third peak wavelength in the wavelength range of 600-630 nm.

In further embodiments, the plurality of light generating devices may comprise a fourth light generating device. The fourth light generating device may be configured to provide fourth radiation having a fourth peak wavelength in the wavelength range of 200-400 nm, especially with a peak in one or more of: the range of 370-395 nm, the range of 280-320 nm, and the range of 200-240 nm, especially a peak in the range of 370-395 nm, or especially a peak in the range of 280-320 nm, or especially a peak in the range of 200-240 nm.

In specific embodiments, $E_2/E_{1>0.005}$, and the fourth peak wavelength has a peak in the range of 370-395 nm.

In further embodiments, the fourth light generating device may be configured to provide fourth radiation having a fourth peak wavelength in the wavelength range of 200-400 nm with a peak in the range of 280-320 nm. In such embodiments, the total spectral power in the range of 280-320 nm may be between 0.4% and 400% of the spectral power emitted between 400 nm and 700 nm (preferably between 4% and 400%, even more preferably 40% and 400%). In particular, some arthropods (crickets, yellow mealworm) have been shown to produce vitamins D2 and D3 when exposed to radiation in the range of 280-320 nm.

In embodiments, two or more of the first light generating device, the second light generating device, the third light generating device, and the fourth light generating device may be the same device. For example, one device may be configured to provide both the first radiation and the second radiation. For instance, the device may comprise a light source and one or more phosphors, wherein the light source generated light source light, and wherein the one or more phosphors convert the light source light into one or more of the first radiation and the second radiation.

In further embodiments, the plurality of light generating devices may comprise a fifth light generating device, wherein the fifth light generating device is configured to provide deep red light. The fifth light generating device may especially comprise a direct solid state light source (e.g. an LED with a peak wavelength of 660 nm), or a blue pumped phosphor, such as MGF. In further embodiments, the fifth light generating device may provide fifth radiation having a fifth peak wavelength in the range of 780-1000 nm.

In specific embodiments, the light generating system may comprise at least five different types of light generating devices, each configured to individually address primarily one of $E_2$, $E_S$, $E_M$, $E_L$, and $E_7$.

In embodiments, the plurality of light generating devices may (each) have an Ingress Protection (IP) rating of at least IP 65, such as at least IP 68.

In embodiments, the light generating system may further comprise a control system. The control system may be configured to control the light generating system, especially to control each light generating device of the plurality of light generating devices.

The term "controlling" and similar terms herein may especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system. The control system and the element may thus at least temporarily, or permanently, functionally be coupled. The element may comprise the control system. In embodiments, the control system and the element may not be physically coupled. Control can be done via wired and/or wireless control. The term "control system" may also refer to a plurality of different control systems, which especially are functionally coupled, and of which e.g. one control system may be a master control system and one or more others may be slave control systems.

In embodiments, the light generating system may have an electrical design allowing the plurality of light sources to be powered individually, but with such a combination of light generating devices in a plurality of channels that with all of the channels fully powered, the light generating system provides system light having the spectral power distribution.

In further embodiments, the light generating system may comprise a driver functionally coupled to one or more of the plurality of light generating devices, wherein the driver is configured to facilitate dimming of the one or more of the plurality of light generating devices, preferably to about 1% of full output power. In further embodiments, the dimmer may be functionally coupled to the control system, and more especially wherein the control system can individually dim different light generating devices.

In embodiments, the light generating system may further comprise a sensor. The sensor may be configured to detect ambient light, and especially to provide a related light signal to the control system. The term " . . . -related signal" may herein refer to a signal that is related to the detected parameter, such as to detected ambient light. In particular, the related signal may comprise raw and/or processed data related to the detected parameter.

In a second operational mode, the control system may be configured to control the system light in dependence of the ambient light, especially in dependence of the related light signal. In particular, the control system may, during the second operational mode, control the system light such that the system light and the ambient light together provide the spectral power distribution, especially at a pre-set light level selected from the range of 0.5-5000 lux, especially from the range of 0.5-2000 lux, and especially to the arthropod hosting space.

Note that for a arthropod hosting space that receives daylight, during sunny days over at least part of the time additional lighting may not be necessary. However, at the beginning of the day or at the end of the day, and/or when one desires to extend the "day period", additional lighting may be provided to reach the pre-set light level, such as at least about 500 lux.

In embodiments, the light-generating system may further comprise a behavioral sensor. The behavioral sensor may be configured to detect an arthropod activity and to provide a related behavioral signal to the control system. The control system may be configured to control the system light based on the behavioral signal, especially wherein the control system is configured to control (the ratio of) $E_M$ and $E_S$ in dependence on the behavioral signal. In particular, the behavioral sensor may sense feeding or movement activity of the arthropod and the control system may control the system light based on this information. Examples of control actions can be to change the spectrum to promote feeding when no or too low feeding activity is sensed (increase $E_S$) or to change the lighting when all provided feed has been consumed and (feeding) activity should no longer be promoted (change from high $E_S$ to (relatively) high $E_M$). Further, movement may be measured and the light level or spectrum may be modified to introduce dynamic effects to induce or reduce movement. Further, by increasing or decreasing light level, or suitable changes in spectrum, areas of (too) high or (too) low animal density can be made lower or higher by locally using negative or positive phototaxis.

In embodiments, the light-generating system may comprise a biometric sensor. The biometric sensor may be configured to determine a biometric parameter, especially one or more of body size (distribution) weight (distribution), and development stage of the arthropod(s), and may provide a biometric signal to the control system. The control system may be configured to control the system light based on the biometric signal.

In embodiments, the system may comprise an environmental sensor. The environmental sensor may be configured to detect an environmental parameter and to provide a related environmental signal to the control system, especially wherein the environmental parameter is selected from the group comprising a temperature, a salinity, and a (relative) humidity. In particular, the environmental parameter may relate to the environment the arthropod is exposed to, such as a temperature and/or a salinity of water in a water basin in which a shrimp is farmed, or such as a temperature and a (relative) humidity of air in a cage in which grasshoppers are farmed. The control system may be configured to control the system light based on the environmental signal, especially wherein the control system is configured to control (the ratio of) $E_M$ and $E_S$ in dependence on the environmental signal, or especially wherein the control system is configured to control (the ratio of) $E_6$ and $E_S$ in dependence on the environmental signal. In particular, the environmental sensor may sense an abiotic parameter in the arthropod hosting space, such as temperature, salinity, and (relative) humidity, and the control system may adapt the settings for one or more of photoperiod, light levels or spectral composition in order to achieve a desired effect in the animal. The desired effect may, for example, be accelerating growth, or keeping growth constant.

In further embodiments, the light generating system may comprise a presence sensor, configured to detect the presence of an object, especially an animal, such as a human, and especially to provide a related object signal to the control system. In such embodiments, the control system may be configured to control the system light based on the object signal. For example, the system light may comprise a relatively large amount of UV light, which may be harmful to humans, and the system may be configured to (automatically) reduce the radiation in the UV range if a human comes near the arthropod hosting space.

In specific embodiments, the light generating system may have the following characteristics: it may comprise one or a combination of solid state light sources, emitting in the range between 400 and 700 nm, comprising a wavelength range S, corresponding to the peak wavelength of a first non-visual/cerebral/extraretinal photoreceptor (with opsin CRY1) plus or minus half its FWHM, which is between 400 nm and 480 nm (440 nm+/−40 nm) and a wavelength range M, corresponding to the peak wavelength of a second non-visual/cerebral/extraretinal photoreceptor (with opsin opnG) plus or minus half its FWHM, which is between (480 nm and 580 nm) (530 nm+/−50 nm). The ratio of the radiation emitted in range M and the radiation emitted in range S, $R_{MS}$, may be at least 2, preferably at least 2.4 and may be less than 30, preferably less than 20, even more preferably less than 10. Relative to the radiation emitted between 360 nm and 780 nm, the radiation emitted between 580 nm and 700 nm (range L), $P_L$, may be smaller than 40%, preferably smaller than 25%, even more preferably smaller than 11% and may be more than 0.2%, preferably more than 5%. If the fraction in range L is larger than 40%, the ratio between the radiation emitted between 620 nm and 700 nm (range deep red, DR), relative to that in range S, $R_{LS}$, may preferably be between 4 and 10, even more preferably between 6 and 8, with a peak in the radiation in the longer wavelengths between 650 nm and 690 nm (to cater for photosynthesis by 'co-located' organisms). Relative to the radiation emitted between 360 nm and 780 nm, the radiation emitted between 360 nm and 400 nm may be less than 0.5%. Relative to the radiation emitted between 360 nm and 780 nm, the radiation emitted between 700 nm and 780 nm may be equal to or less than 2.2%. All radiation levels and ratios mentioned herein may refer to energy in W unless specified otherwise.

In a second aspect, the invention may provide an arthropod keeping system. The arthropod keeping system may comprise an arthropod hosting space and the light generating system of the invention. The arthropod hosting space may be configured for hosting arthropods. The light generating system may especially be configured to provide system light to the arthropod hosting space.

In embodiments, the arthropod hosting space may especially comprise one or more of a water basin, a tank, a cage, a crate, a box, a tube or hose, a field (of grass), a plant, and a (part of a) water body. It will be clear to the person skilled in the art what kind of hosting space would be suitable for the to-be-farmed arthropod.

In a further aspect, the invention may provide a method for arthropod keeping. The method may comprise providing system light to an arthropod, wherein the system light has the spectral power distribution. In embodiments, the system light may be provided with the light generating system of the invention. However, the method is not limited to such embodiments.

In embodiments, the arthropod may be an immature arthropod or an adult arthropod, especially an immature arthropod, or especially an adult arthropod. In general, immature arthropods may be of primary interest for keeping, while adult arthropods are primarily used for reproduction. However, the adult arthropod may (epigenetically) pass on its biological clock to its offspring. Hence, it may be beneficial to expose the adult arthropods to similar lighting as the as the immature arthropods, especially to expose the adult arthropods to the same system light as the immature arthropods, or especially to expose the adult arthropods to the same temporal pattern as the immature arthropods.

In further embodiments, the method may comprise providing the system light according to a repeating temporal pattern (also see above). The temporal pattern may have a pattern duration $T_p$ selected from the range of 12-24 hours, and the temporal pattern may comprise a photoperiod and a dark period. The photoperiod may have a photoperiod duration $T_d$, especially wherein $0.45 \leq T_d/T_p \leq 0.65$. The method may further comprise: providing the system light at an intensity selected from the range of 0.5-2000 lux during the photoperiod; and providing the system light at an intensity selected from the range of 0-0.5 lux during the dark period.

In embodiments, the method may comprise one or more of: (i) detecting an arthropod activity, providing a related behavioral signal, and controlling the system light based on the behavioral signal; and determining an environmental parameter, providing a related environmental signal, and, controlling the system light based on the environmental signal, wherein the environmental parameter is selected from the group comprising a temperature, a salinity, and a humidity.

In a further aspect, the invention may provide a computer program product comprising instructions for execution on a computer functionally coupled to a light generating system, wherein the instructions, when executed by the computer, cause the light generating system to carry out the method according to the invention.

In a further aspect, the invention may provide a data carrier, carrying thereupon program instructions which, when executed by a computer functionally coupled to a light generating system, cause the light generating system to carry out the method of the invention.

The term "light source" may also relate to a plurality of light sources, such as 2-20 (solid state) LED light sources. Hence, the term LED may also refer to a plurality of LEDs.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF THE EMBODIMENTS

Figure 1:
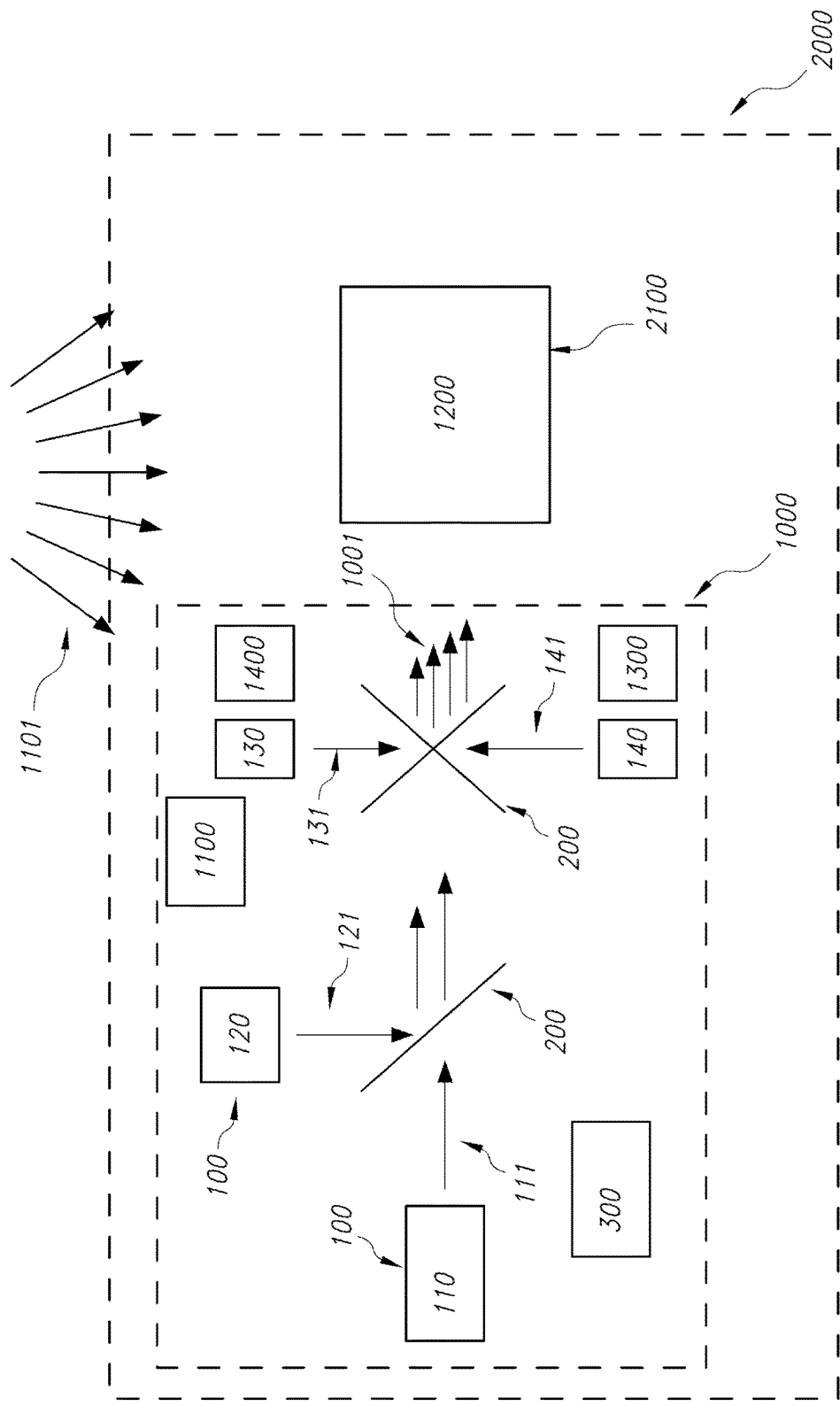
FIG. 1 schematically depicts embodiments of the light generating system, the arthropod keeping system and the method of the invention.

FIG. 1 schematically depicts a light generating system 1000 for arthropod keeping. In the depicted embodiment, the light generating system is configured to generate system light 1001, and especially to provide the system light 1001 to an arthropod hosting space 1200. In a first operational mode, the light generating system 1000 is configured to provide the system light 1001 having a spectral power distribution, wherein the spectral power distribution comprises: a first spectral power $E_1$ in a first wavelength range of 360-780 nm; a second spectral power $E_2$ in a second wavelength range of 360-400 nm; a third spectral power $E_S$ in a third wavelength range of 400-480 nm; a fourth spectral power $E_M$ in a fourth wavelength range of 480-580 nm; a fifth spectral power $E_L$ in a fifth wavelength range of 580-700 nm; a sixth spectral power $E_6$ in a sixth wavelength range of 620-700 nm; and a seventh spectral power $E_7$ in a seventh wavelength range of 700-780 nm; wherein $1.75 \leq E_M/E_S \leq 20$; $E_2/E_1 \leq 0.005$; $E_7/E_1 \leq 0.022$; and (i) $E_L/E_1 \leq 0.3$; or (ii) $0.3 < E_L/E_1 \leq 0.8$, and $3.4 \leq E_6/E_S \leq 14$, and wherein the sixth wavelength range comprises a peak between 650-690 nm.

In embodiments, the light generating system 1000 may comprise a light generating device 100, especially a plurality of light generating devices 100. In further embodiments, the first light generating device 110 may be configured to provide first radiation 111 having a first peak wavelength in the wavelength range of 420-480 nm. In further embodiments, the second light generating device 120 may be configured to provide second radiation 121 having a second peak wavelength in the wavelength range of 500-560 nm. In further embodiments, the third light generating device 130 may be configured to provide third radiation 131 having a third peak wavelength in the wavelength range of 570-600 nm. In further embodiments, the fourth light generating device 140 may be configured to provide fourth radiation 141 having a fourth peak wavelength in the wavelength range of 200-400 nm.

In further embodiments, the plurality of light generating devices 100 may comprise one or more of a first light generating device 110, a second light generating device 120, a third light generating device 130 and a fourth light generating device 140. For instance, the plurality of light generating devices may comprise a fight light generating device, a second light generating device, and one or more of a third light generating device and a fourth light generating device.

In the depicted embodiment, the light generating system 1000 comprises a plurality of light generating devices 100, wherein the plurality of light generating devices 100 comprises a first light generating device 110, a second light generating device 120, a third light generating device 130 and a fourth light generating device 140. Together, the plurality of light generating devices 100 may provide the system light 1000. In particular, reference 200 may indicate an optical element 200 arranged to combine the radiation of the different light generating devices 100 to provide the system light 1001.

In the depicted embodiment, the light generating system 1000 further comprises a control system 300. The control system 300 may especially be configured to control (each of) the plurality of light generating devices 100.

The light generating system further comprises an (ambient light) sensor 1100, wherein the sensor 1100 is configured to detect ambient light 1101, and especially to provide a related light signal to the control system 300. In a second operational mode, the control system 300 may be configured to control the system light 1001 in dependence of the ambient light 1101, wherein the system light 1001 and the ambient light 1101 together provide the spectral power distribution (to the arthropod hosting space 1200). Hence, the sensor 1100 may detect ambient light 1101, such as sunlight, and may report data related to one or more of the spectral composition and/or the intensity of the ambient light 1101 to the control system 300. The control system 300 may then be configured to determine a suitable spectral composition of the system light 1001 such that the system light 1001 and the ambient light 1101 together provide the spectral power distribution. In particular, the control system 300 may further control the light generating devices 100 in order to provide the system light having the suitable spectral composition.

In further embodiments, the control system may control the system light 1001 in dependence of the ambient light 1101 such that the system light 1001 and the ambient light 1001 may together provide the spectral power distribution at a pre-defined light level selected from the range of 0.5-2000 lux.

In the depicted embodiment, the system 1000 further comprises a behavioral sensor 1300, wherein the behavioral sensor 1300 is configured to detect an arthropod activity and to provide a related behavioral signal to the control system 300. The control system 300 may especially be configured to control the system light 1001 based on the behavioral signal.

FIG. 1 further schematically depicts an embodiment of the arthropod keeping system 2000. The arthropod keeping system comprises an arthropod hosting space 1200 and the light generating system 1000. The arthropod hosting space 1200 may be configured for hosting arthropods. The light generating system 1000 may be configured to provide system light 1001 to the arthropod hosting space 1200. In the depicted embodiment, the arthropod hosting space 1200 may especially comprise a water basin 2100.

FIG. 1 further schematically depicts a method for arthropod keeping, wherein the method comprises providing system light 1001 to an arthropod, especially to an arthropod in the arthropod hosting space 1200, wherein the system light 1001 has the spectral power distribution. In particular, in the depicted embodiment, the method may comprise providing the system light 1001 with the light generating system 1000.

Figure 2:
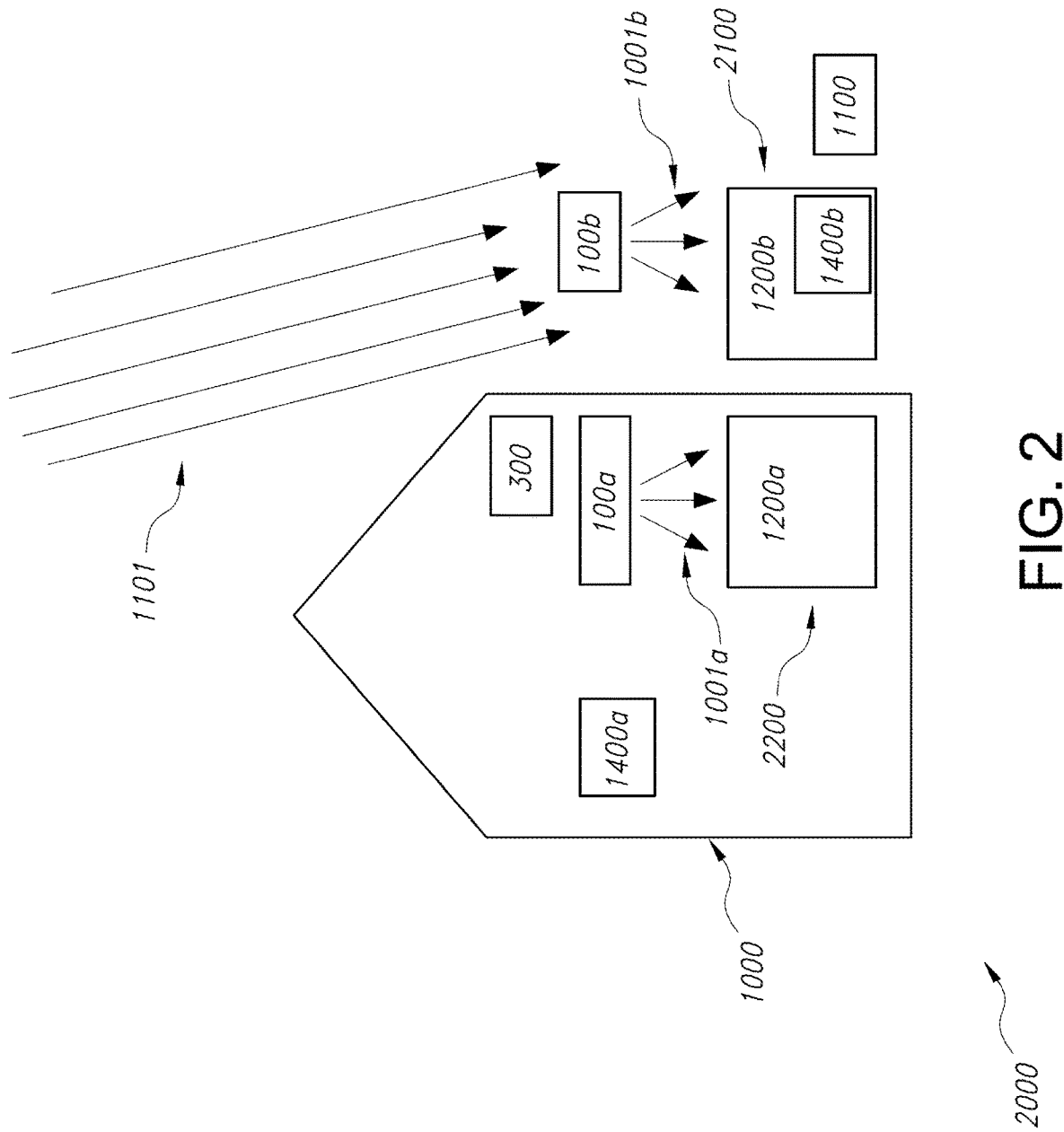
FIG. 2 schematically depicts an embodiment of the arthropod keeping system.

FIG. 2 schematically depicts an embodiment of the arthropod keeping system 2000. In the depicted embodiment, the arthropod keeping system 2000 comprises two arthropod hosting spaces 1200. In particular, a first arthropod hosting space 1200a may be arranged inside of a building, and may comprise a cage 2200, whereas a second arthropod hosting space 1200b may be arranged outside, and may comprise a water basin 2100. Hence, the arthropod keeping system 2000 may be configured for hosting multiple arthropod species.

In the depicted embodiment, the light generating system 1000 comprises an environmental sensor 1400, wherein the environmental sensor 1400 is configured to detect an environmental parameter and to provide a related environmental signal to the control system 300. The environmental parameter may especially be selected from the group comprising a temperature, a salinity, and a humidity. The control system 300 may be configured to control the system light 1001 based on the environmental signal.

In particular, the light generating system 1000 comprises a first environmental sensor 1400a configured to detect an environmental parameter of the environment the arthropods in the first arthropod hosting space 1200a are exposed to, such as one or more of a temperature and a relative humidity of the air in the building. Further, the light generating system 1000 may comprise a second environmental sensor 1400b configured to detect an environmental parameter of the environment the arthropods in the second arthropod hosting space 1200b are exposed to, such as one or more of a temperature and a salinity of the water in the water basin 2100.

Further, in the depicted embodiment, the first arthropod hosting space 1200a may be relatively shielded from ambient light 1101 and may essentially only receive first system light 1001a, especially wherein a first plurality of light generating devices 100a provides first system light 1001a having the spectral power distribution. However, the second arthropod hosting space 1200b may receive both ambient light 1101 and second system light 1001b. Hence, the light generating system 1000 may comprise a (light) sensor 1100 configured to detect the ambient light 1101, wherein the control system 300 is configured to control a second plurality of light sources 100b to provide the second system light 1001b based on the ambient light 1101 such that the second system light 1001b and the ambient light 1101 together provide the spectral power distribution to the second arthropod hosting space 1200.

Figure 3:
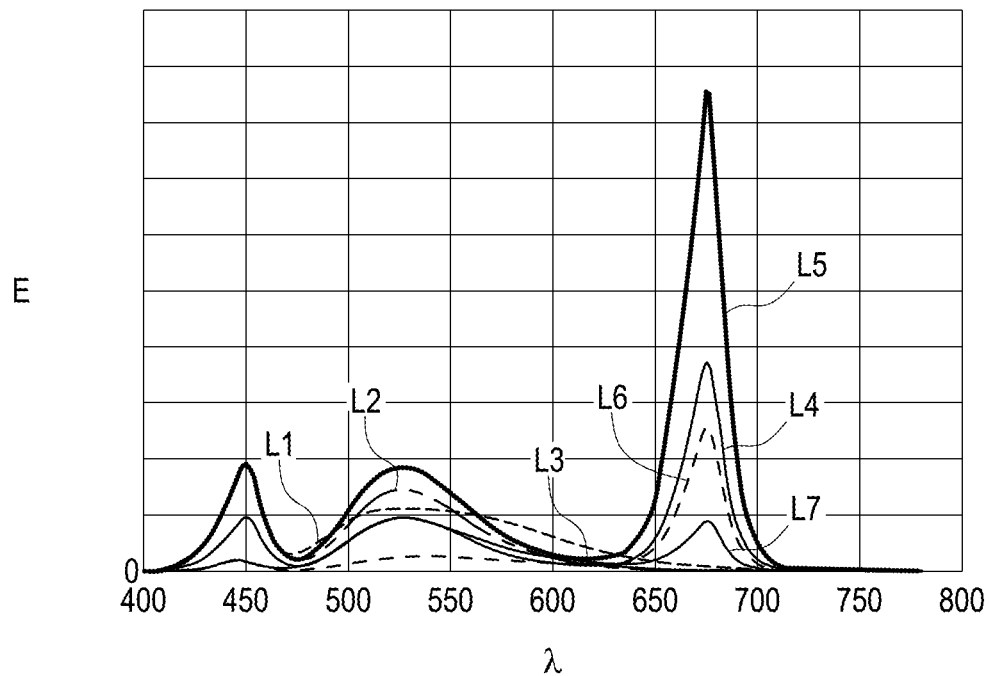
FIG. 3 schematically depicts example spectral power distributions.

FIG. 3A schematically depict example spectral power distributions, wherein each of the lines L1-L7 depict spectral power E (in a.u., though on an energy scale, like e.g. Watts) vs wavelength λ of a different example spectral power distribution. Characteristics of the depicted spectral power distributions and the light sources that can provide them, as well as of several other spectral power distributions, are summarized in the tables below, with the first table indicating the light source and the spectral power distribution, and the second table indicating the associated spectral properties:

| Nr | x | y | CCT [K] | Duv | Ra | R9 |
|----|---|---|---------|-----|----|----|
| L1 | 0.2852 | 0.3596 | 7750 | 0.0314 | 66 | −99 |
| L2 | 0.2284 | 0.3691 | 11000 | 0.0648 | 44 | −228 |
| L3 | 0.2355 | 0.4033 | 9500 | 0.0716 | 43 | −237 |
| L4 | 0.2829 | 0.3905 | 7500 | 0.0449 | 69 | 51 |
|    | 0.2893 | 0.3916 | 7000 | 0.0424 | 69 | 25 |
| L6 | 0.39152 | 0.41118 | 4000 | 0.0122 | 71 | −60 |
| L7 | 0.3134 | 0.5360 | 5800 | 0.0795 | 51 | −114 |
| L8 | 0.2309 | 0.4362 | 9000 | 0.0835 | 22 | −316 |
| L9 | 0.2486 | 0.4724 | 8000 | 0.0860 | 36 | 18 |
| L10 | 0.3289 | 0.4203 | 5700 | 0.0368 | 66 | −83 |
| L11 | 0.3680 | 0.4063 | 4600 | 0.0171 | 80 | 40 |
| L12 | 0.4186 | 0.4008 | 3300 | 0.0016 | 77 | 4.6 |
| L13 | 0.4193 | 0.4167 | 3400 | 0.0080 | 58 | −136 |
| L14 | 0.3376 | 0.4765 | 5500 | 0.0538 | 71 | 32 |

Figure 4:
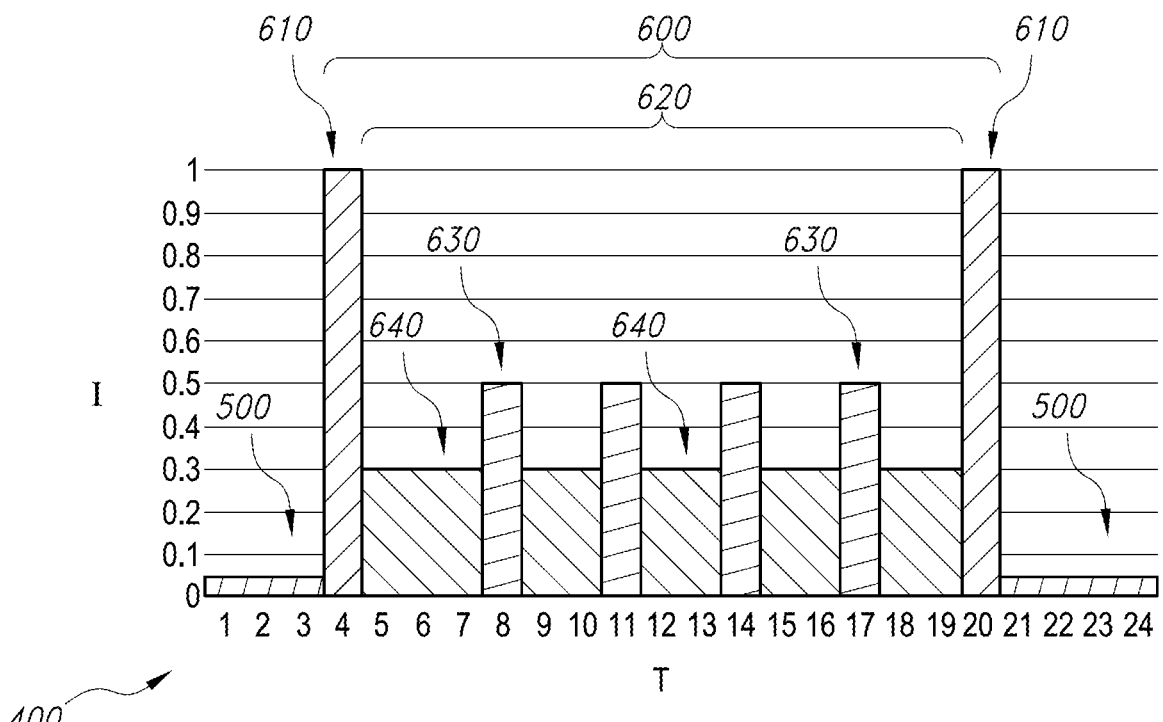
FIG. 4 schematically depicts an embodiment of the temporal pattern.

FIG. 4 schematically depicts an embodiment of a repeating temporal pattern 400 with intensity I (in a.u.) versus time T (in hours). In particular, FIG. 4 may schematically depict a single repetition or subunit of the repeating temporal pattern 400.

The temporal pattern 400 comprises a photoperiod 600 and a dark period 500, especially wherein during the photoperiod 600 the light generating system 1000 is configured to generate the system light 1001 at an intensity selected from the range of 0.5-2000 lux, and wherein during the dark period 500 the light generating system 1000 is configured to generate the system light 1001 at an intensity selected from the range of 0-0.5 lux. The temporal pattern 400 may have a pattern duration $T_p$ selected from the range of 12-24 hours, especially 24 hours in the depicted embodiment. Further, the photoperiod 600 may a photoperiod duration $T_d$, wherein $0.40 \leq T_d/T_p \leq 0.75$.

In the depicted embodiment, the photoperiod 600 comprises one or more first photoperiods 610 and one or more second photoperiods 620, wherein the one or more first photoperiods 610 and the one or more second photoperiods 620 alternate. The one or more first photoperiods 610 are temporally arranged at one or more of the beginning and the end of the photoperiod 600, here especially both at the beginning and the end of the photoperiod 600, wherein a single second photoperiod 620 separates the two first photoperiods 610. The one or more first photoperiods 610 may have a duration selected from the range of 10-90 minutes, wherein the one or more second photoperiods 620 may have a duration selected from the range of 10-1080 minutes. During the one or more first photoperiods 610, the light generating system 1000 may generate the system light 1001 at a first intensity $I_1$, and during the second photoperiod 620

| Nr | Light source | $E_M/E_S$ | $E_L/E_1$ | $E_7/E_1$ | $E_6/E_S$ |
|----|--------------|-----------|-----------|-----------|-----------|
| L1 | Blue LED, 450 nm, YAG phosphor | 1.92 | 0.20 | 0.0042 | |
| L2 | Blue LED, 450 nm, BOSE phosphor | 2.00 | 0.079 | 0.0 | |
| L3 | Blue LED, 450 nm, BOSE phosphor | 2.45 | 0.084 | 0 | |
| L4 | Blue LED, 450 nm, BOSE phosphor, LED 680 nm | 2.45 | 0.53 | 0.008 | 3.80 |
|    | Blue LED 450 nm, Green phosphor BOSE, Red LED 680 nm | 2.50 | 0.56 | 0.01 | 4.37 |
| L6 | Cool white LED, Green phosphor BOSE, Red LED 680 nm | 3.50 | 0.72 | 0.0005 | 11.4 |
| L7 | Cool white LED, Green phosphor BOSE, Red LED, 680 nm | 9.63 | 0.33 | 0.0005 | 3.91 |
| L8 | Blue LED, 450 nm, Green LED 540 nm, amber LED 590 nm | 2.32 | 0.064 | 7 10$^{-5}$ | |
| L9 | Blue LED, 450 nm, Green LED 540 nm, LED 680 nm | 3.14 | 0.49 | 0.0082 | 6.00 |
| L10 | Cool white LED, 5000K, BOSE phosphor | 3.00 | 0.27 | 0.0015 | |
| L11 | Cool white, BOSE phosphor, Red LED 680 nm | 3.00 | 0.63 | 0.00075 | 6.06 |
| L12 | Blue LED 450 nm, Lime phosphor, Red LED 660 nm | 3.00 | 0.63 | 0.0010 | 5.79 |
| L13 | Blue LED 450 nm, LuAG phosphor, Red LED 660 nm | 5.00 | 0.40 | 0.00054 | 11.66 |
| L14 | Blue LED 450 nm, GAL phosphor, Red LED 660 nm | 6.50 | 0.39 | 0.00072 | 3.56 | the light generating system 1000 may generate the system light 1001 at a second intensity $I_2$, wherein $1.5 \leq I_1/I_2 \leq 1000$.

In the depicted embodiment, the photoperiod 600, especially the second photoperiod 620, further comprises alternating feeding periods 630 and non-feeding periods 640. The feeding periods 630 may have a duration selected from the range of 10-60 min. The non-feeding periods 640 may have a duration selected from the range of 60-300 min. In particular, $E_M/E_S$ may be lower during the feeding period 630 than during the non-feeding period 640. In embodiments, as in the depicted embodiment, also the intensity of the system light (1001) may be higher during the feeding period 630 than during the non-feeding period 640.

Herein, x and y are the color coordinates according to the CIE 1931 color space, CCT indicates the correlated color temperature, Duv indicates the distance from the black body line in UV color space, Ra or CRI is the color rendering index, and R9 indicates the color rendering index for reference color 9 (Red).

The term "plurality" refers to two or more. Furthermore, the terms "a plurality of" and "a number of" may be used interchangeably.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%. Moreover, the terms "about" and "approximately" may also relate to 90% or higher, such as 95% or higher, especially 99% or higher, even more especially 99.5% or higher, including 100%. For numerical values it is to be understood that the terms "substantially", "essentially", "about", and "approximately" may also relate to the range of 90%-110%, such as 95%-105%, especially 99%-101% of the values(s) it refers to.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

The term "further embodiment" and similar terms may refer to an embodiment comprising the features of the previously discussed embodiment, but may also refer to an alternative embodiment.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", "include", "including", "contain", "containing" and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings. Moreover, if a method or an embodiment of the method is described being executed in a device, apparatus, or system, it will be understood that the device, apparatus, or system is suitable for or configured for (executing) the method or the embodiment of the method, respectively.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating system for arthropod keeping comprising:
   a plurality of light generating devices configured to generate system light provided to an arthropod hosting space, wherein in a first operational mode the light generating system is configured to provide the system light having a spectral power distribution, wherein the spectral power distribution comprises:
   a first spectral power $E_1$ in a first wavelength range of 360-780 nm;
   a second spectral power $E_2$ in a second wavelength range of 360-400 nm;
   a third spectral power $E_S$ in a third wavelength range of 400-480 nm;

a fourth spectral power $E_M$ in a fourth wavelength range of 480-580 nm;
a fifth spectral power $E_L$ in a fifth wavelength range of 580-700 nm;
a sixth spectral power $E_6$ in a sixth wavelength range of 620-700 nm;
a seventh spectral power $E_7$ in a seventh wavelength range of 700-780 nm;
and wherein:
$1.75 \leq E_M/E_S \leq 20$; $E_2/E_1 \leq 0.005$; $E_7/E_1 \leq 0.022$; and either
(i) $E_L/E_1 \leq 0.3$; or
(ii) $0.3 < E_L/E_1 \leq 0.8$, $3.4 \leq E_6/E_S \leq 14$, and the sixth wavelength range comprises a peak between 650-690 nm.

2. The light generating system according to claim 1, wherein the first operational mode comprises a repeating temporal pattern, wherein the temporal pattern comprises a photoperiod and a dark period, wherein during the photoperiod the light generating system is configured to generate the system light at an intensity selected from the range of 0.5-2000 lux, and wherein during the dark period the light generating system is configured to generate the system light at an intensity selected from the range of 0-0.5 lux, wherein the temporal pattern has a pattern duration $T_p$ selected from the range of 12-24 hours, and wherein the photoperiod has a photoperiod duration $T_d$, wherein $0.40 \leq T_d/T_p \leq 0.75$.

3. The light generating system according to claim 2, wherein the photoperiod comprises alternating feeding periods and non-feeding periods, wherein the feeding periods have a duration selected from the range of 10-60 min, and wherein the non-feeding periods have a duration selected from the range of 60-300 min, wherein $E_M/E_S$ is lower during the feeding period than during the non-feeding period.

4. The light generating system according to claim 2, wherein the photoperiod comprises one or more first photoperiods and one or more second photoperiods, wherein the one or more first photoperiods and the one or more second photoperiods alternate, and wherein the one or more first photoperiods are temporally arranged at one or more of the beginning and the end of the photoperiod, wherein the one or more first photoperiods have a duration selected from the range of 10-90 minutes, wherein the one or more second photoperiods have a duration selected from the range of 10-1080 minutes and wherein during the one or more first photoperiods, the light generating system may generate the system light at a first intensity $I_1$, and during the second photoperiod the light generating system may generate the system light at a second intensity $I_2$, wherein $1.5 \leq I_1/I_2 \leq 1000$.

5. The light generating system according to claim 1, wherein the plurality of light generating devices comprises a first light generating device, a second light generating device, and one or more of a third light generating device and a fourth light generating device; wherein the first light generating device is configured to provide first radiation having a first peak wavelength in the wavelength range of 420-480 nm, wherein the second light generating device is configured to provide second radiation having a second peak wavelength in the wavelength range of 500-560 nm, wherein the third light generating device is configured to provide third radiation having a third peak wavelength in the wavelength range of 570-600 nm, and wherein the fourth light generating device is configured to provide fourth radiation having a fourth peak wavelength in the wavelength range of 200-400 nm, and wherein $2 \leq E_M/E_S \leq 10$.

6. The light generating system according to claim 1, wherein the light generating system further comprises a sensor and a control system, wherein the sensor is configured to detect ambient light, and wherein in a second operational mode the control system is configured to control the system light in dependence of the ambient light, wherein the system light and the ambient light together provide the spectral power distribution at a pre-set light level selected from the range of 0.5-2000 lux.

7. The light generating system according to claim 6, wherein the control system is configured to individually control each light generating device of the plurality of light generating devices.

8. The light generating system according to claim 6, wherein one or more applies of:
the light generating system further comprises a behavioral sensor, wherein the behavioral sensor is configured to detect an arthropod activity and to provide a related behavioral signal to the control system, wherein the control system is configured to control the system light based on the behavioral signal; and
the light generating system further comprises an environmental sensor, wherein the environmental sensor is configured to detect an environmental parameter and to provide a related environmental signal to the control system, wherein the environmental parameter is selected from the group comprising a temperature, a salinity, and a humidity, and wherein the control system is configured to control the system light based on the environmental signal.

9. An arthropod keeping system comprising an arthropod hosting space and the light generating system according to claim 1, wherein the arthropod hosting space is configured for hosting arthropods, and wherein the light generating system is configured to provide system light to the arthropod hosting space.

10. A method for arthropod keeping, wherein the method comprises providing system light to an arthropod, using a light generating system for arthropod keeping, configured to generate the system light, wherein in a first operational mode the light generating system is configured to provide the system light having a spectral power distribution, wherein the spectral power distribution comprises:
a first spectral power $E_1$ in a first wavelength range of 360-780 nm;
a second spectral power $E_2$ in a second wavelength range of 360-400 nm;
a third spectral power $E_S$ in a third wavelength range of 400-480 nm;
a fourth spectral power $E_M$ in a fourth wavelength range of 480-580 nm;
a fifth spectral power $E_L$ in a fifth wavelength range of 580-700 nm;
a sixth spectral power $E_6$ in a sixth wavelength range of 620-700 nm;
a seventh spectral power $E_7$ in a seventh wavelength range of 700-780 nm;
and wherein:
$1.75 \leq E_M/E_S \leq 20$; $E_2/E_1 \leq 0.005$; $E_7/E_1 \leq 0.022$; and either
(i) $E_L/E_1 \leq 0.3$; or
(ii) $0.3 < E_L/E_1 \leq 0.8$, $3.4 \leq E_6/E_S \leq 14$, and the sixth wavelength range comprises a peak between 650-690 nm.

11. The method according to claim 10, wherein the arthropod is an adult arthropod, and wherein the method comprises providing the system light according to a repeating temporal pattern, wherein the temporal pattern has a pattern duration $T_p$ selected from the range of 12-24 hours, wherein the temporal pattern comprises a photoperiod and a dark period, and wherein the photoperiod has a photoperiod duration Ta, wherein $0.45 \leq T_d/T_p \leq 0.65$, and wherein the method comprises:

provide the system light at an intensity selected from the range of 0.5-2000 lux during the photoperiod; and
providing the system light at an intensity selected from the range of 0-0.5 lux during the dark period.

12. The method according to claim 10, wherein the method comprises one or more of:

detecting an arthropod activity, providing a related behavioral signal, and controlling the system light based on the behavioral signal; and determining an environmental parameter, providing a related environmental signal, and, controlling the system light based on the environmental signal, wherein the environmental parameter is selected from the group comprising a temperature, a salinity, and a humidity.

13. The method according to claim 10, wherein the method comprises providing the system light with the light generating system.

14. The method according to claim 10, wherein the arthropod comprises a species selected from the group comprising Crustacea and Hexapoda.

15. A computer readable medium comprising instructions for execution on a computer functionally coupled to a light generating system, wherein the instructions, when executed by the computer, cause the light generating system to carry out the method according to claim 10.

* * * * *